(12) United States Patent
Patwardhan

(10) Patent No.: US 11,278,236 B2
(45) Date of Patent: Mar. 22, 2022

(54) IMAGING-BASED METHODS AND APPARATUSES FOR ASSESSING SKIN PIGMENTATION

(71) Applicant: Canfield Scientific, Incorporated, Parsippany, NJ (US)

(72) Inventor: Sachin V. Patwardhan, Mount Tabor, NJ (US)

(73) Assignee: Canfield Scientific, Incorporated, Parsippany, NJ (US)

( * ) Notice: Subject to any disclaimer, the term of this patent is extended or adjusted under 35 U.S.C. 154(b) by 92 days.

(21) Appl. No.: 16/374,608

(22) Filed: Apr. 3, 2019

(65) Prior Publication Data
US 2019/0298252 A1 Oct. 3, 2019

Related U.S. Application Data

(60) Provisional application No. 62/652,291, filed on Apr. 3, 2018.

(51) Int. Cl.
*A61B 5/00* (2006.01)
*G06T 7/00* (2017.01)

(52) U.S. Cl.
CPC ............ *A61B 5/443* (2013.01); *A61B 5/0077* (2013.01); *A61B 5/742* (2013.01); *G06T 7/0012* (2013.01); *G06T 2207/10024* (2013.01); *G06T 2207/30088* (2013.01)

(58) Field of Classification Search
None
See application file for complete search history.

(56) References Cited

U.S. PATENT DOCUMENTS

| 8,498,460 | B2 | 7/2013 | Patwardhan | |
|---|---|---|---|---|
| 9,898,818 | B2* | 2/2018 | Jayasundera | ............ G06T 7/254 |
| 2005/0265585 | A1* | 12/2005 | Rowe | ................. G06K 9/00046 |
| | | | | 382/124 |
| 2008/0049990 | A1* | 2/2008 | Melchi | ................... A61B 5/445 |
| | | | | 382/128 |
| 2009/0137908 | A1* | 5/2009 | Patwardhan | ......... A61B 5/0071 |
| | | | | 600/476 |
| 2011/0206254 | A1* | 8/2011 | Patwardhan | ......... A61B 5/0077 |
| | | | | 382/128 |
| 2015/0025343 | A1* | 1/2015 | Gareau | ................ A61B 5/0075 |
| | | | | 600/328 |

(Continued)

OTHER PUBLICATIONS

I. Hamzavi et al., Parametric Modeling of Narrowband UV-B Phototherapy for Vitiligo Using a Novel Quantitative Tool, Arch. Dermatol., vol. 140, Jun. 2004, pp. 677-683.

(Continued)

*Primary Examiner* — Jiangeng Sun

(57) ABSTRACT

Methods and apparatuses are disclosed for assessing pigmentation of skin based on images thereof. In disclosed implementations, a cross-polarized blue image of skin is obtained and processed to extract pigment distribution information. Useful applications include assessing depigmentation, as in the skin condition vitiligo, as well as assessing re-pigmentation such as due to treatment. In addition to the spatial extent of depigmentation, implementations of the present disclosure can also provide the degree of depigmentation. The degree and area of depigmentation can be measured with better accuracy and sensitivity than known techniques.

19 Claims, 20 Drawing Sheets

(56) References Cited

U.S. PATENT DOCUMENTS

2016/0166194 A1* 6/2016 Gareau ................. A61B 5/443
                                                           600/328
2017/0124709 A1* 5/2017 Rithe ................... G06K 9/2036
2018/0235534 A1* 8/2018 Gareau ................. A61B 5/444
2018/0279943 A1* 10/2018 Budman ............... G06T 7/0014

OTHER PUBLICATIONS

I. Kohli et al., Three-dimensional imaging of vitiligo, Experimental Dermatology, 2015, 24, pp. 879-880.

* cited by examiner

FIG. 5A
FIG. 5B
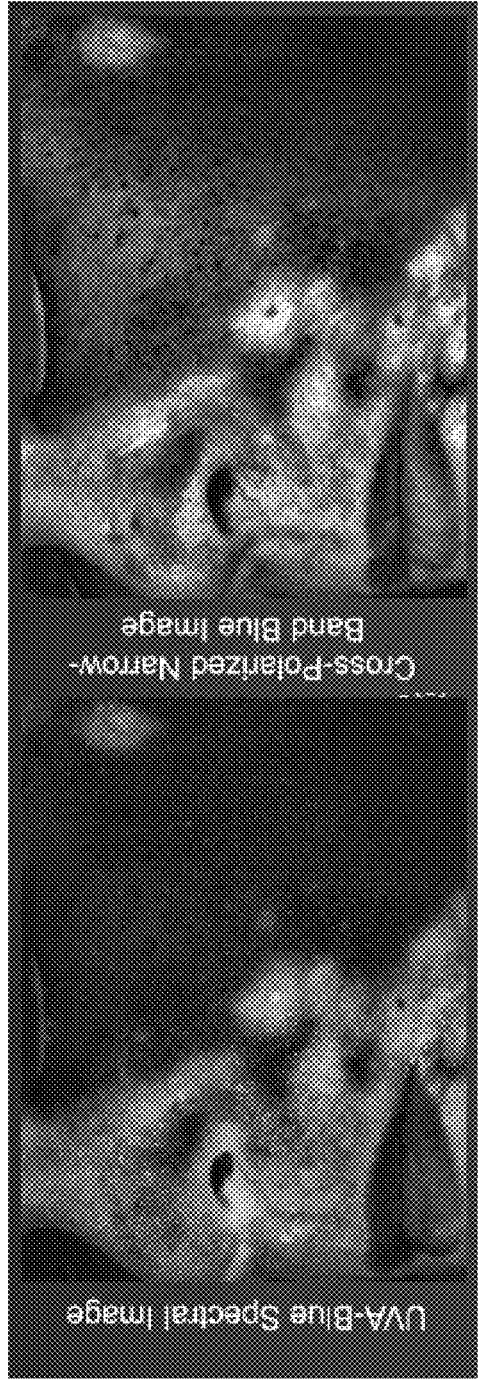
FIG. 5C
FIG. 5D

FIG. 6A
FIG. 6B
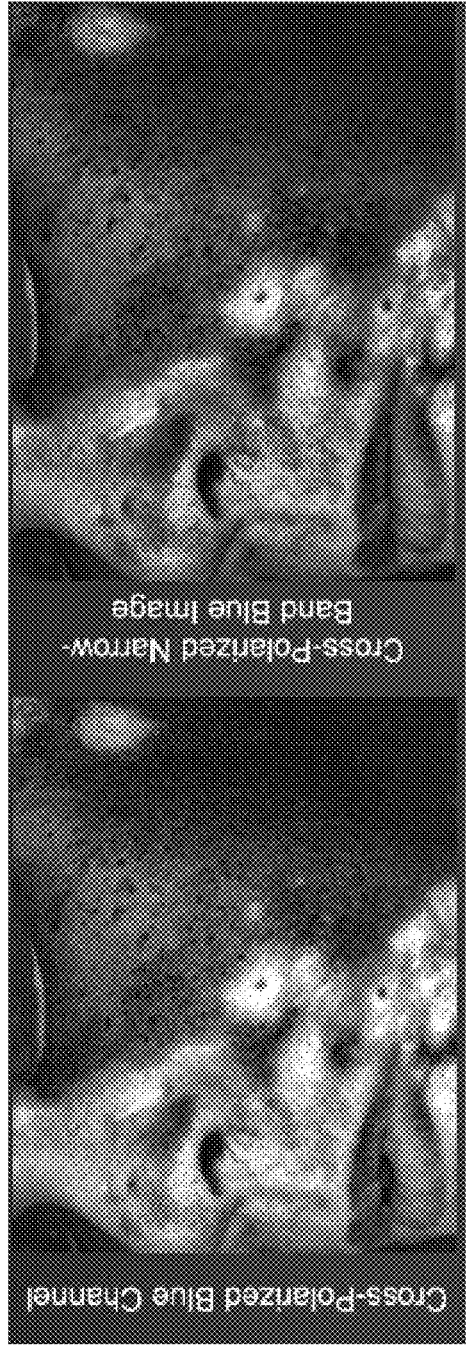
FIG. 6C
FIG. 6D

FIG. 11A
FIG. 11B
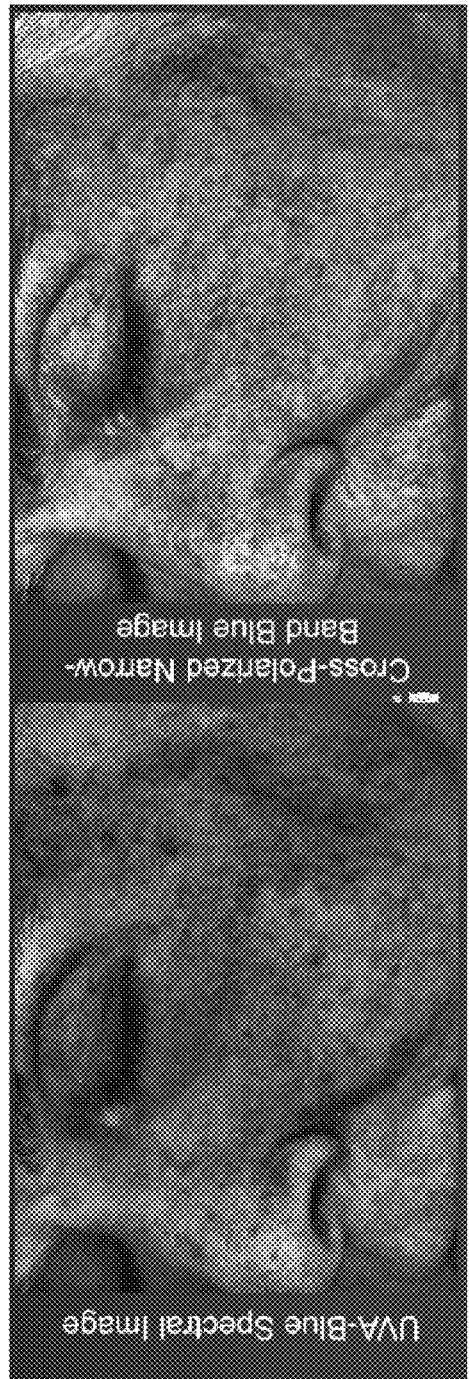
FIG. 11C
FIG. 11D

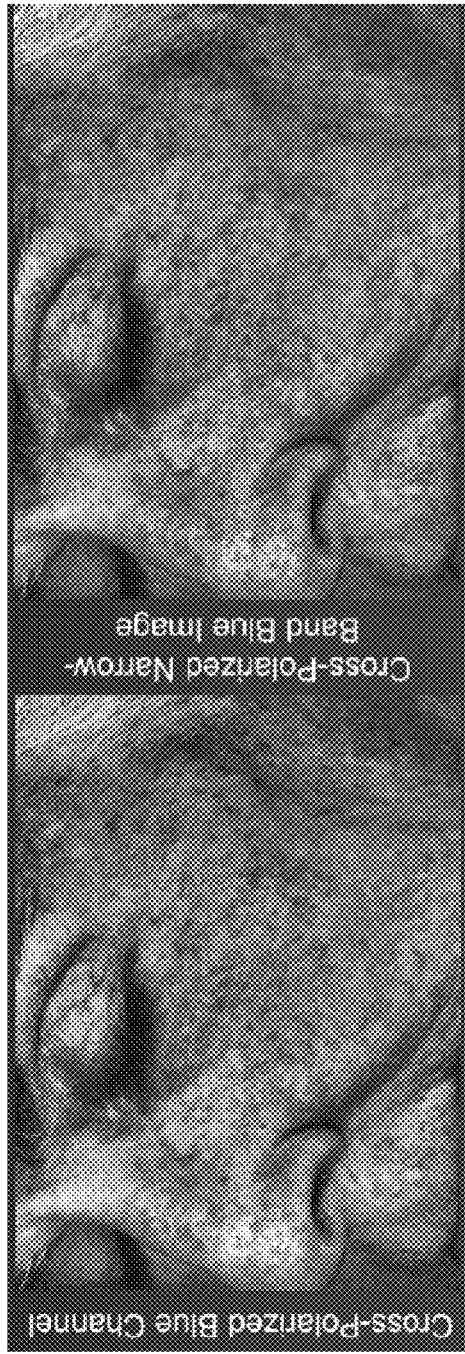
FIG. 12A  Clinical Image
FIG. 12B  Cross-Polarized Image
FIG. 12C  Cross-Polarized Blue Channel
FIG. 12D  Cross-Polarized Narrow-Band Blue Image

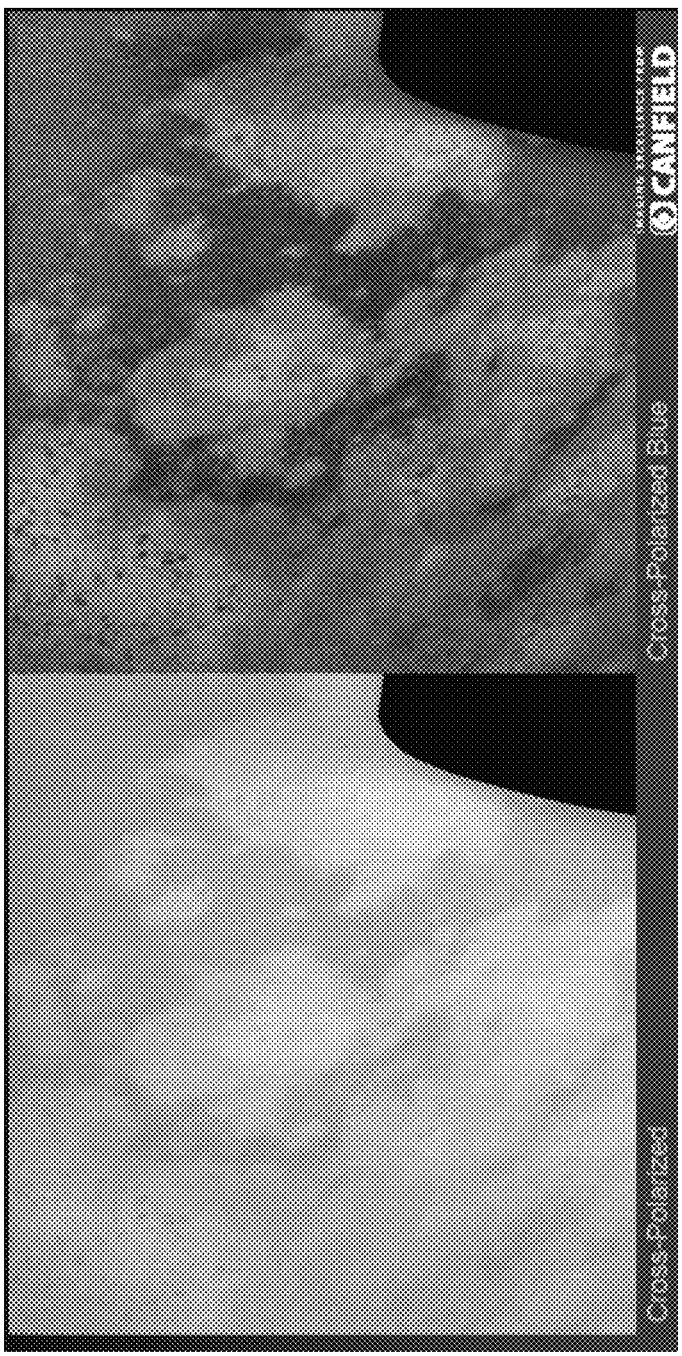
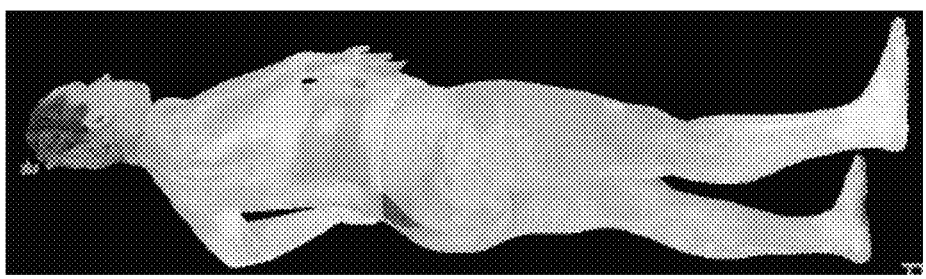
FIG. 15A  FIG. 15B  FIG. 15C

IMAGING-BASED METHODS AND APPARATUSES FOR ASSESSING SKIN PIGMENTATION

RELATED APPLICATIONS

This application claims priority from U.S. Provisional Patent Application No. 62/652,291, filed Apr. 3, 2018 and incorporated herein by reference in its entirety.

BACKGROUND INFORMATION

Vitiligo is a skin disorder that results from the loss of pigmentation due to the destruction of melanocytes. It affects 1-2% of the world's population and affects all skin types. Although there have been several qualitative and semiquantitative measures that have been used to assess the condition and treatment outcomes, there is no standardized method to determine the treatment efficacy for vitiligo.

The Vitiligo Area Scoring Index (VASI) is a quantitative clinical tool that is currently used to evaluate vitiligo parametrically. In accordance with VASI methodology, the sizes of vitiligo lesions are estimated in units of hands, with the assumption that the area of a person's palm is approximately 1% of their body surface area. The level of depigmentation in each lesion is then assessed a percentage of 0, 10%, 25%, 50%, 75%, 90%, or 100%. Palm units and this percentage are multiplied to generate a score for that lesion. The process is repeated for each lesion on a body part and the scores for the lesions added to generate a score for the body part. As an example, if the upper thigh has a vitiligo lesion that is 1.5 times the size of the palm and the pigmentation level is 50%, then its VASI score is 1.5×0.5=0.75. Measurements are done over the entire body (except the face) and the VASI scores for all body parts are added as the total score for the subject. For the face, a similar technique is used but the measurement unit of size is the thumb.

Clearly, the VASI method is non-repetitive and suffers from considerable inter- and intra-evaluator variability. Also, in many cases, the VASI method lacks sufficient sensitivity to effectively measure re-pigmentation, such as may be due to treatment.

For cases in which the evaluator is unsure about lesion boundaries or pigmentation levels, a Wood's lamp can be used, with room lights off, when viewing a subject's skin. A Wood's Lamp is a source of UVA illumination, with a center wavelength around 360 nm and a bandwidth of +/−30-40 nm. The subject's skin is illuminated with this source as the clinician looks at it through a viewing window. The equivalent of what the clinician sees can be captured by camera in a UVA image. Like human eyes, which cannot see UV light, the typical camera sensor has a UV blocking filter in front of the sensor. Presumably, the areas of skin that appear dark are pigmented areas, with melanin. Both melanin and hemoglobin, however, have high degrees of absorption in this spectral band, in which case hemoglobin-based features (such as vasculature, erythema/inflammation) will also appear dark under UVA illumination.

Another disadvantage of evaluating pigmentation under UVA illumination is that multiple endogenous fluorophores (such as collagen, flavins, elastin, NADH, tryptophan, lipopigments, pyridoxine, porphyrins, etc.) are excited in this spectral band and produce fluorescence. The emission signals from these fluorophores can obscure pigmentation information, change perceived pigmentation levels, or hinder identifying the true boundaries of de-pigmented areas.

SUMMARY OF THE DISCLOSURE

The present disclosure sets out a method of assessing pigmentation of skin comprising: obtaining a cross-polarized image of skin; determining a level of a pigment of the skin; determining an area in which the level of the pigment is above a threshold; generating at least one of a metric indicative of the level of the pigment or a metric indicative of the area; and causing the at least one metric to be displayed, stored, transmitted or further processed.

The present disclosure also sets out an apparatus for assessing pigmentation of skin comprising: a storage device containing instructions; and a processor executing the instructions to: obtain a cross-polarized image of skin; determine a level of a pigment of the skin; determine an area in which the level of the pigment is above a threshold; generate at least one of a metric indicative of the level of the pigment or a metric indicative of the area; and cause the at least one metric to be displayed, stored, transmitted or further processed.

These and other aspects of such apparatuses and methods and exemplary variants thereof are described in greater detail below.

BRIEF DESCRIPTION OF THE DRAWINGS

FIGS. 5A-5D show enlarged duplicates of the images of FIGS. 4A-4D, respectively, enlarged to show only the region of interest (ROI) indicated in FIG. 4A.

FIGS. 6A-6D show a group of images of the ROI obtained in accordance with the present disclosure.

FIGS. 11A-11D show enlarged duplicates of the images of FIG. 10 enlarged to show only the region of interest (ROI) indicated in FIG. 10.

FIGS. 12A-12D show a group of images of the second subject obtained in accordance with the present disclosure.

FIG. 15A shows a whole-body, cross-polarized white-light, three-dimensional model of a third subject; FIG. 15B shows an image of a portion of the model; and FIG. 15C shows the blue channel of the image of FIG. 15B.

DETAILED DESCRIPTION

Figure 1:
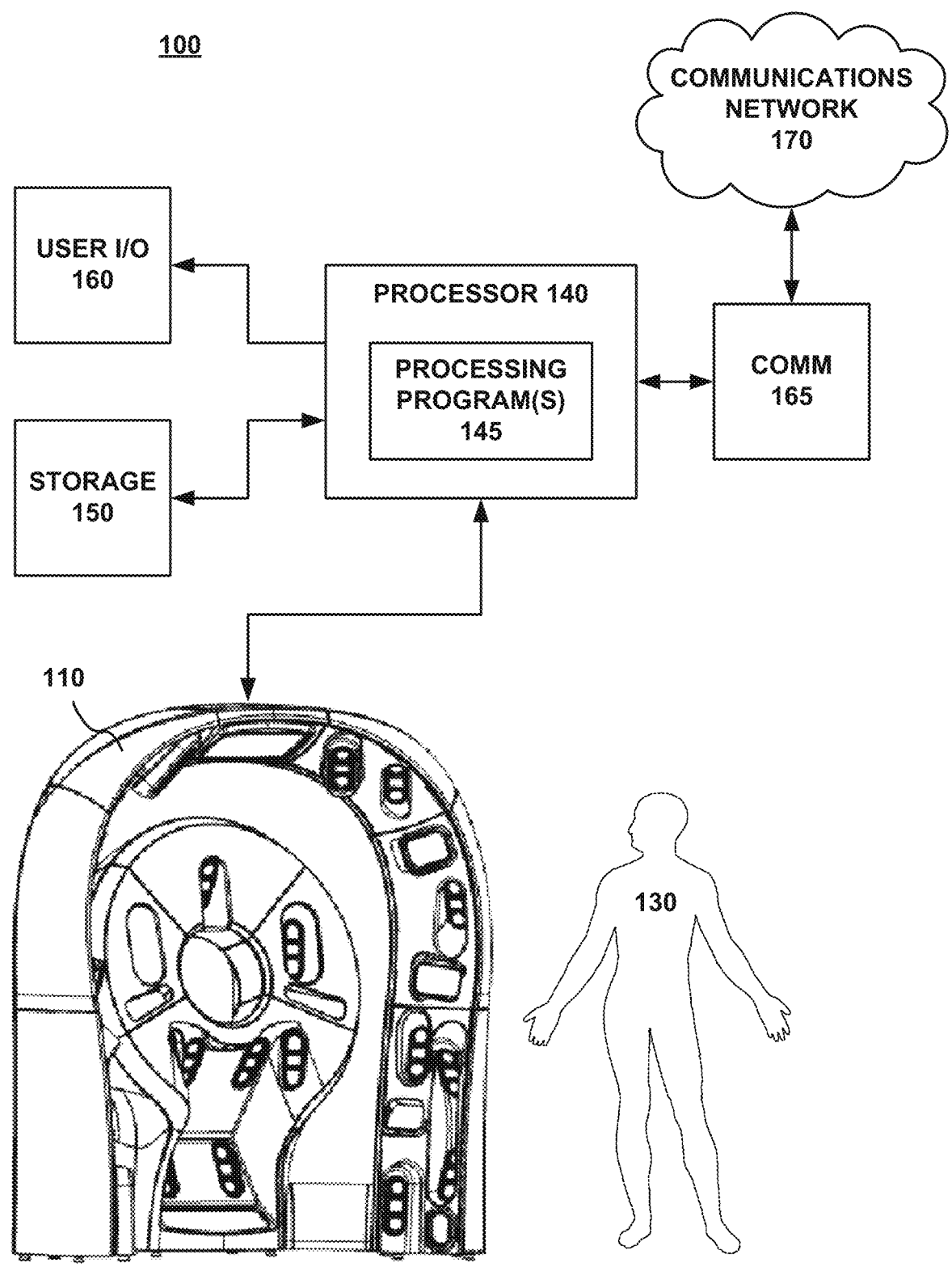
FIG. 1 is a schematic representation of an exemplary system in accordance with the present disclosure.

The following merely illustrates the principles of the present disclosure. It will thus be appreciated that those skilled in the art will be able to devise various arrangements which, although not explicitly described or shown herein, embody the principles of the disclosure and are included within its spirit and scope. More particularly, while numerous specific details are set forth, it is understood that embodiments of the disclosure may be practiced without these specific details and in other instances, well-known circuits, structures, and techniques have not been shown in order not to obscure the understanding of this disclosure.

Furthermore, all examples and conditional language recited herein are principally intended expressly to be only for pedagogical purposes to aid the reader in understanding the principles of the disclosure and the concepts contributed by the inventor(s) to furthering the art and are to be construed as being without limitation to such specifically recited examples and conditions.

Moreover, all statements herein reciting principles, aspects, and embodiments of the disclosure, as well as specific examples thereof, are intended to encompass both structural and functional equivalents thereof. Additionally, it is intended that such equivalents include both currently-known equivalents as well as equivalents developed in the future, i.e., any elements developed that perform the same function, regardless of structure.

Thus, for example, it will be appreciated by those skilled in the art that the diagrams herein represent conceptual views of illustrative structures embodying the principles of the disclosure.

In addition, it will be appreciated by those skilled in art that any flowcharts, process diagrams, and the like represent various processes which may be substantially represented in computer readable media and so executed by a computer or processor, whether or not such computer or processor is explicitly shown.

The functions of the various elements shown in the drawings, including any functional blocks, steps, procedures, modules, units or the like may be provided through the use of dedicated hardware as well as hardware capable of executing software in association with appropriate software. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, dedicated circuitry, digital signal processor (DSP) hardware, network-based processors, application specific integrated circuitry (ASIC), read-only memory (ROM), random access memory (RAM), and non-volatile storage. Other hardware, conventional and/or custom, may also be included.

Software modules, or simply modules which are implied to be software, may be represented herein as any combination of flowchart elements or other elements indicating performance of process steps and/or textual description. Such modules may be executed by hardware that is expressly or implicitly shown. Additionally, although illustrated as single elements, each such block or step shown may be implemented with multiple blocks or steps, or various combinations thereof. Terms such as "software," "application," "program," "firmware," or the like, are intended to refer, without limitation, to any instruction or set of instructions, structure, or logic embodied in any suitable machine-readable medium.

As used herein, the term "image" may encompass any form of photo-documentation, including 2D images and/or 3D surfaces and/or 3D volumetric image data, where a 2D image could be a single or a multichannel visible impression obtained by a camera, a 3D surface could be points in a 3D space connected by line segments to form a polygonal mesh along with any associated 2D images that represent the underlying texture, and 3D volumetric image data may represent a stack of 2D images that represent a 3D volume of the object being imaged.

Turning now to the drawings, FIG. 1 schematically depicts an exemplary system 100 for capturing and processing images in accordance with the present disclosure. The major components of system 100 include an imaging apparatus 110 coupled to a processor 140. Imaging apparatus 110 may include a 2D or 3D image capture system for capturing one or more images of all or a portion of a subject 130. The images may be single mode or multimodal, including standard white light, polarized, and/or absorption images, captured at selected wavelengths and/or illuminated at selected wavelengths, in accordance with the present disclosure.

Additionally, as described further below, imaging apparatus 110 is capable of cross-polarized imaging. See U.S. patent application Ser. No. 15/908,169, incorporated herein by reference in its entirety, which describes such apparatuses.

Images captured by imaging apparatus 110 are provided to processor 140 for processing as described in greater detail herein. Processor 140 may also control imaging apparatus 110, such as by controlling the capture of images and/or illumination.

Imaging apparatus 110 may include one or more illumination sources that are activated to illuminate subject 130 directly or through one or more filtering elements. Light reflected or emitted from subject 130 can be captured by apparatus 110 through one or more filtering elements, which may include one or more filters for passing or blocking light of a selected wavelength or band of wavelengths, and/or polarizers, collectively "filters," which can be selectively placed in or out of the respective optical path of the filtering element. Note that the term "light" as used herein is not necessarily limited to humanly visible electromagnetic radiation and may include portions of the electromagnetic spectrum above and below the visible range.

Processor 140 may be implemented, for example, with one or more computers, workstations, central processing units (CPU), microprocessors, or the like, operating in accordance with one or more programs 145 embodied in a compatible non-transient, machine-readable, storage medium. Processor 140 may be coupled to a storage 150 and user input/output devices 160, such as a keyboard, display, pointing device, touchscreen, or the like. Processor 140 may also be connected to a communications interface 165 for wired or wireless connection with a communications network 170, such as the Internet, for receiving and/or transmitting images and data, commands, software updates or the like. Additionally, or alternatively, processor 140 may receive and process images from sources other than imaging apparatus 110.

The link between processor 140 and imaging apparatus 110 may be wired or wireless and may be direct (such as over a Bluetooth or USB connection directly between 140 and 110) or indirect, such as via communications network 170, among other possibilities.

In exemplary implementations, imaging apparatus 110 is of one or more of the VISIA, VECTRA (e.g., VECTRA WB180, WB360 or H1), VEOS (e.g., SLR, DS-3), INTELLISTUDIO, and TWINFLASH (e.g., RL-XP) families of imaging systems from Canfield Scientific, Inc. See, e.g., U.S. patent application Ser. No. 14/193,824 (Publication No. 2014/0243685A1), incorporated herein by reference in its entirety. As can be appreciated, it is contemplated that imaging apparatus 110 is not limited to the aforementioned systems.

An exemplary method 200A in accordance with the present disclosure will now be described with reference to FIG. 2A, which shows a flowchart of method 200A.

Figure 2A:
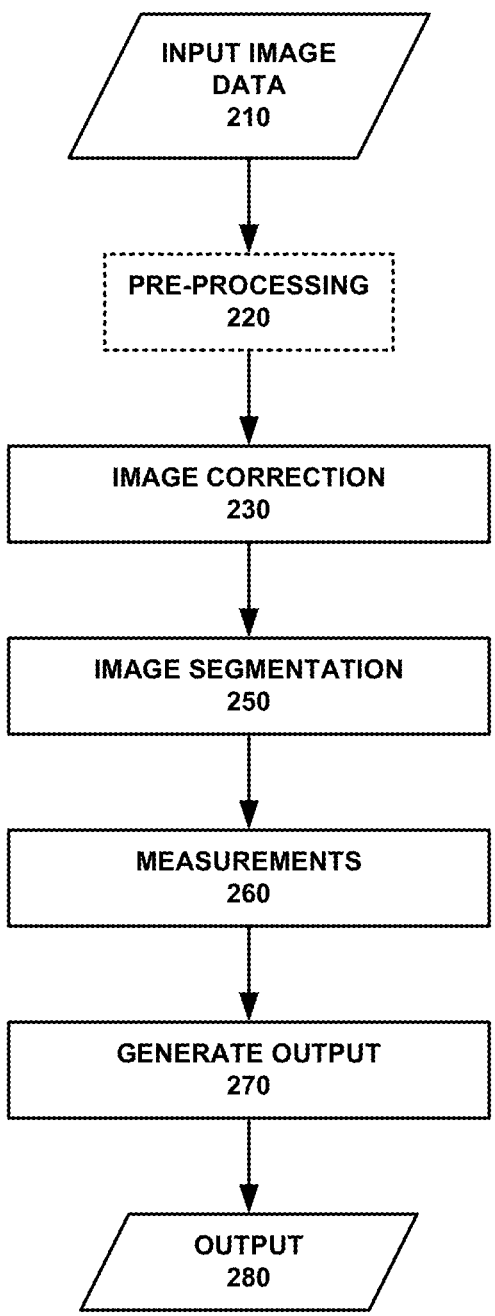
FIGS. 2A-2C are flowcharts of exemplary methods in accordance with the present disclosure.

As shown in FIG. 2A, input image data is obtained at 210. This can include, for example, capturing an input image, such as with imaging apparatus 110, or receiving the input image data at processor 140, configured to carry out method 200A, such as by executing one or more programs 145.

I have discovered that blue, narrow spectral band illumination with wavelengths of approximately 450-470 nm, in a cross-polarized imaging mode, will provide a much cleaner indication of melanin pigmentation in human skin than other imaging modalities. Hemoglobin absorption in this spectral band is significantly lower than that of melanin, and most of the endogenous fluorophores will not be excited and hence will not generate any significant fluorescence. Additionally, by employing cross-polarization imaging—in which the illumination is linearly polarized with a first orientation and the illuminated skin is imaged through a linear polarizer of a second orientation orthogonal to the first orientation—only diffuse reflectance is captured, and hence any skin surface artifacts will not affect evaluation of the imaged skin.

The aforementioned narrow spectral band illumination can be achieved by an appropriate filter arranged in front of a broad-spectrum output source, such as a xenon flash. The narrow spectral band blue is a subset of the visible spectrum. Spectral filtering can also or alternatively be applied before the camera.

Because monochrome sensors are typically capable of higher detail and sensitivity, a monochrome camera with external filtering will likely produce better results than a conventional RGB color camera.

As a cheaper, but less accurate alternative using a conventional RGB color camera, it is possible to capture a cross-polarized image with a broader spectrum illumination (e.g., the entire visible spectrum or white light) and to rely on the blue color Bayer filter typically employed over the camera sensor to act as the narrow spectral band filter. In other words, the pigmentation information that can be obtained from a narrow-band blue cross-polarized image can also be obtained, largely, from the blue channel of a visible spectrum/white light cross-polarized image. With broad spectrum illumination, however, the exposure time and ISO of the image capture should be set lower than in the case of narrow band illumination.

In either case, if a color camera is used to capture the image, only the blue color channel from the RGB image or the blue color channel information directly from the camera raw image data need be used in evaluating pigmentation.

FIGS. 3A-3D show a first group of images of a first subject for illustrating aspects of the present disclosure. The illustrative images shown were captured as RGB images using a digital color camera.

Figures 3A, 3B, 3C, 3D:
FIGS. 3A-3D show a first group of images of a first subject for illustrating aspects of the present disclosure.

FIG. 3B shows an image that was captured by illuminating the subject with UVA light from a Wood's Lamp. This is done by filtering the white light output from a xenon flash with a filter having a central wavelength around 365 nm+/−35 nm. While no filter was applied in front of the camera, the camera has a built-in UV blocking filter on its image sensor.

FIG. 3C shows a UVA-Blue spectral image captured with a broad-band filter in front of a xenon flash that passes both UVA, and visible light up to 500 nm (i.e. 300-500 nm). A filter that blocks all wavelengths shorter than 500 nm is arranged in front of the camera. Most of the colors seen in the images of FIGS. 3B and 3C are due to fluorescence. Also, the filters used in capturing these images are not ideal (there will be light leakage from the stop bands), further contributing to the color.

For the image of FIG. 3D, illumination was provided from a xenon flash filtered with a band pass filter having a center wavelength of −450 nm+/−30 nm (blue light) and polarized by a polarizing filter. A further polarizing filter is arranged to filter the image captured by the camera, the further polarizing filter having an orientation orthogonal to that of the polarizing filter of the illumination source.

In the image of FIG. 3D, with the blue light peak at 450 nm, there is no appreciable fluorescence as in the images of FIGS. 3B and 3C. Moreover, the absorption of blue light by hemoglobin is significantly lower than that of melanin. Additionally, the use of cross-polarization eliminates surface reflections, whereby the camera captures only the diffuse reflection of the blue light that has entered the skin, undergone absorption and scattering, and is reflected back to the camera. A cross-polarized, narrow band blue image, such as that of FIG. 3D, is preferably included as input image data at 210 of method 200A.

Returning now to the flowchart of FIG. 2A, the image data input at 210 can be pre-processed at 220 for noise removal, brightness enhancement, contrast enhancement, or the like.

Figures 4A, 4B, 4C, 4D:
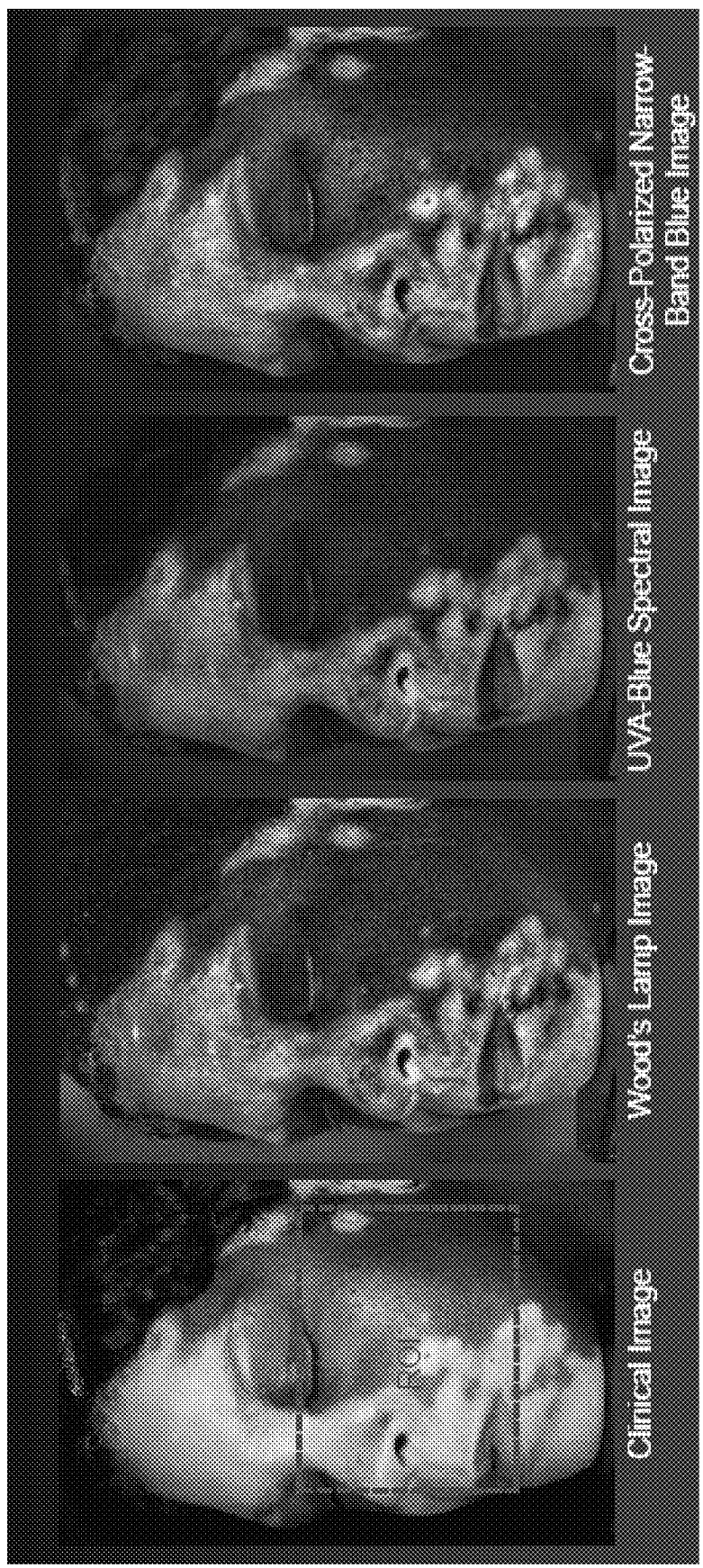
FIGS. 4A-4D show a second group of images derived from the images of FIGS. 3A-3D.

FIGS. 4A-4D show a second group of images derived from the images of FIGS. 3A-3D, respectively. FIG. 4A shows the same RGB image as FIG. 3A, whereas the images of FIGS. 4B-4D are grayscale representations of the blue channel of the respective images of FIGS. 3B-3D. Additionally, in the images of FIGS. 4B-4D, the blue channel from the respective images of FIGS. 3B-3D is enhanced for contrast. This can be achieved, for example, at 220 by transforming the pixel values using contrast-limited adaptive histogram equalization (CLAHE).

It is also possible to perform noise filtering at 220 by applying linear filters, median filters, or adaptive filters, such as a Wiener filter, on the input image data.

FIGS. 5A-5D show enlarged duplicates of the images of FIGS. 4A-4D, respectively, enlarged to show only the region of interest (ROI) indicated in FIG. 4A.

FIG. 6B shows a cross-polarized image of the ROI indicated in FIG. 4A, also shown enlarged in FIG. 6A, under white-light illumination. FIG. 6C shows the blue channel of the cross-polarized white-light image shown in FIG. 6B. For comparison, the cross-polarized, narrow-band blue image is shown next to it in FIG. 6D.

After pre-processing at 220, the input image data is preferably subjected to a correction operation at 230 in order to correct for the distribution of illumination used to capture the input image. In an exemplary embodiment, such an operation entails capturing an image of a white standard target using the same system and conditions used to capture the input image. This white standard image serves as a measure of input light intensity and its distribution. The input image data is then normalized (e.g., divided) by the white standard image to provide input image data that is calibrated for absorption.

Figure 8B:
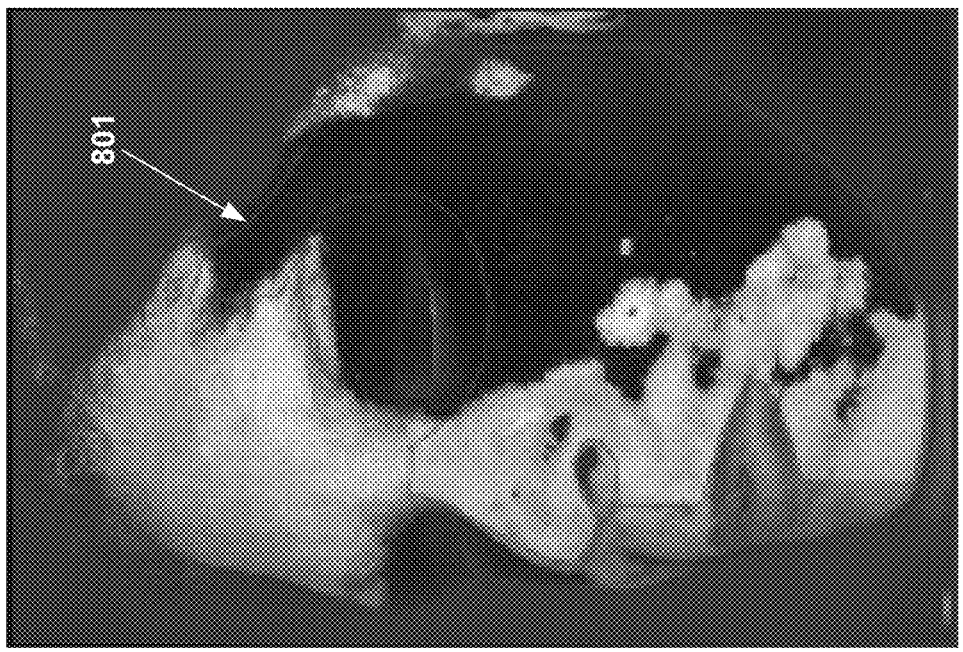
FIG. 8B shows the processed input image further processed to indicate areas of depigmentation detected in accordance with the present disclosure.
Figure 8A:
FIG. 8A shows a processed input image.

At 250, depigmented, pigmented, and areas re-pigmented due to treatment can be detected by performing a segmentation operation using the input image data corrected at 230. The corrected image and its segmentation are illustrated in FIGS. 8A and 8B, respectively. FIG. 8B shows the image of FIG. 8A processed to indicate areas of depigmentation detected within a selected region 801 of the image. The region 801 can be defined by user input or automatically generated based on facial features, such as the eyes, nose, lips, chin, ears, scalp, etc.

In an exemplary embodiment, the image of FIG. 8B is generated by comparing the intensity of pixels within region 801 to a threshold value and identifying all the pixels whose intensity is higher than the threshold value as depigmented skin, typically due to vitiligo. These pixels that are brighter than the threshold value are brightened, or have a color added, such as yellow for example, to provide an accentuated visual indication of depigmented skin, as detected hereby. In exemplary implementations, the threshold value can be determined in one or more ways, such as by computing the threshold value using the intensity distribution of all the pixels inside region 801 by statistical means such as a Bayesian classification technique, or by Otsu's thresholding method, for example.

At 260, area measurements and intensity measurements indicating levels of pigmentation, depigmentation, and/or re-pigmentation due to treatment can be performed using segmented images, such as that shown in FIG. 8B. For example, the level of depigmentation at a pixel of the image can be determined as a function of the intensity of the pixel. The intensities of pixels in one or more regions of the image can be averaged to provide a depigmentation metric for the one or more regions. If the captured images are 3D (such as those captured with Canfield Scientific's VECTRA) true surface area measurements can be obtained. The measurements can be presented in a variety of alphanumeric, graphical or visual formats. An area metric indicative of the depigmentation area measurement, an intensity metric indicative of the depigmentation intensity measurement, and/or a combination of the area and intensity metrics (e.g., a product thereof) can be generated and presented, among other possibilities.

Additionally, the intensity of the illumination used in capturing the input images is preferably known and/or set to a predetermined value so that measurements can be standardized. The illumination intensity can be controlled in a variety of known ways, such as by setting the charging level of a flash light source which generates the illumination, whether broad spectrum or narrow band blue, used in capturing the input images. Additionally, or alternatively, a light meter can be used to measure the illumination intensity, which can be used, for example, to normalize the pigmentation intensity measurements.

As can be appreciated, the accuracy and sensitivity of the area and intensity measurements possible with the disclosed methods are significantly better than those provided by the VASI technique.

At 270, further images can be generated and presented to indicate: pigmentation levels, such as in a contour or heat map; boundaries between normal skin, lesions, and re-pigmentation areas; and/or other information that may be useful to the user. For example, a heat map image (see, e.g., FIG. 19) can be generated by modifying the colors of those pixels indicative of depigmentation in the segmented images based on the pixels' brightness, with the brightest pixels shown as red, the next brightest pixels shown as yellow, the next brightest pixels shown as green, and the least brightest of said pixels shown as blue. For further granularity, shades of red, yellow, green and blue can also be used.

The input images, such as the clinical image (standard photograph) of the subject, and/or any final or intermediate images processed as described above may be provided as output 280, such as for display to a user, for visual assessment.

As can be appreciated, the detection and evaluation of vitiligo is dependent on skin type, as the depigmentation that characterizes vitiligo is more readily evident in dark skin as compared to light skin. As such, the imaging and image analysis parameters can be tuned, preferably, based on the subject's skin type, or baseline level of pigmentation (i.e., lightness/darkness). For example, image capture parameters such illumination intensity, exposure time, and ISO may be adjusted based on skin type. One or more threshold values used for image segmentation at 250 can be adjusted based on skin type. In exemplary implementations, for the same illumination intensity and camera capture parameters, the threshold values for segmenting depigmented skin are preferably set lower for darker skin subjects compared to lighter skin subjects. Alternatively, the illumination intensity can be increased when capturing images of a darker skin subject without changing the segmenting threshold values.

An exemplary method 200B in accordance with the present disclosure will now be described with reference to FIG. 2B, which shows a flowchart of method 200B.

Figure 2B:
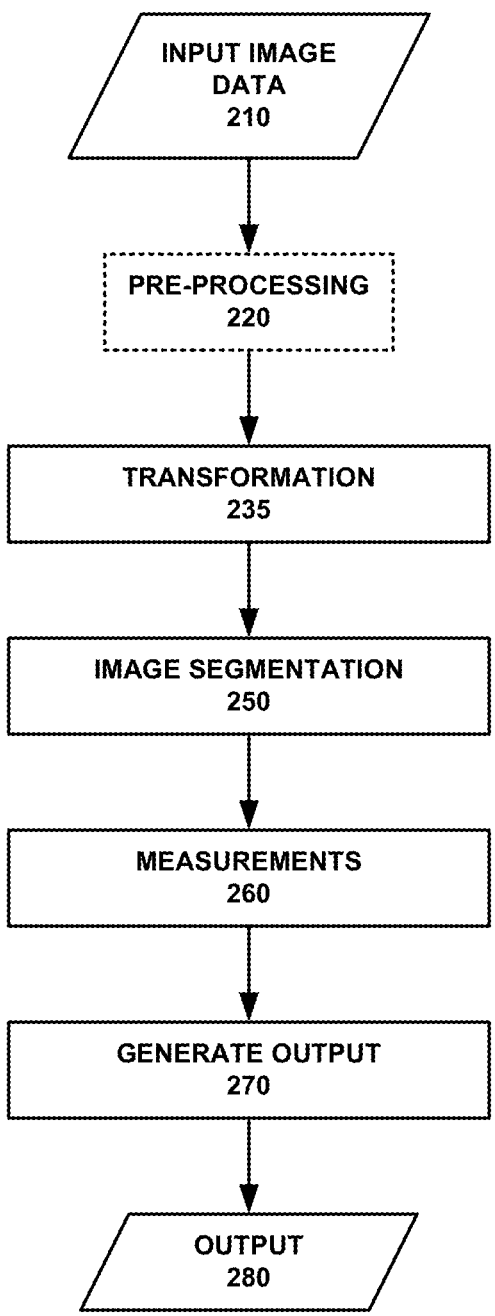

As shown in FIG. 2B, input image data is obtained at 210. In the case of method 200B, the input image data includes a broad spectrum (white-light, RGB) cross-polarized image of the subject, such as shown in FIG. 6B. While cross-polarized broad spectrum images are preferable, unpolarized broad spectrum images can be used if cross-polarized images are not available.

Returning now to the flowchart of FIG. 2B, as in method 200A, the image data input at 210 can be pre-processed at 220 for noise removal, brightness enhancement, contrast enhancement, or the like.

After pre-processing at 220, the input image data can be subjected to one or more transformations at 235 in order to assess the distribution of pigmentation, such as due to melanin, and hemoglobin. The RGB input images may be transformed at 235 to other color spaces, such as the lab color space, for example.

In exemplary embodiments, an RBX transformation can be performed at 235. As described in U.S. Pat. No. 8,498, 460, incorporated herein by reference in its entirety, images indicative of melanin and hemoglobin distribution and concentration can be generated from a broad-band, color cross-polarized image, such as that of FIG. 6B, using the RBX transformation.

Figures 7A, 7B, 7C, 7D:
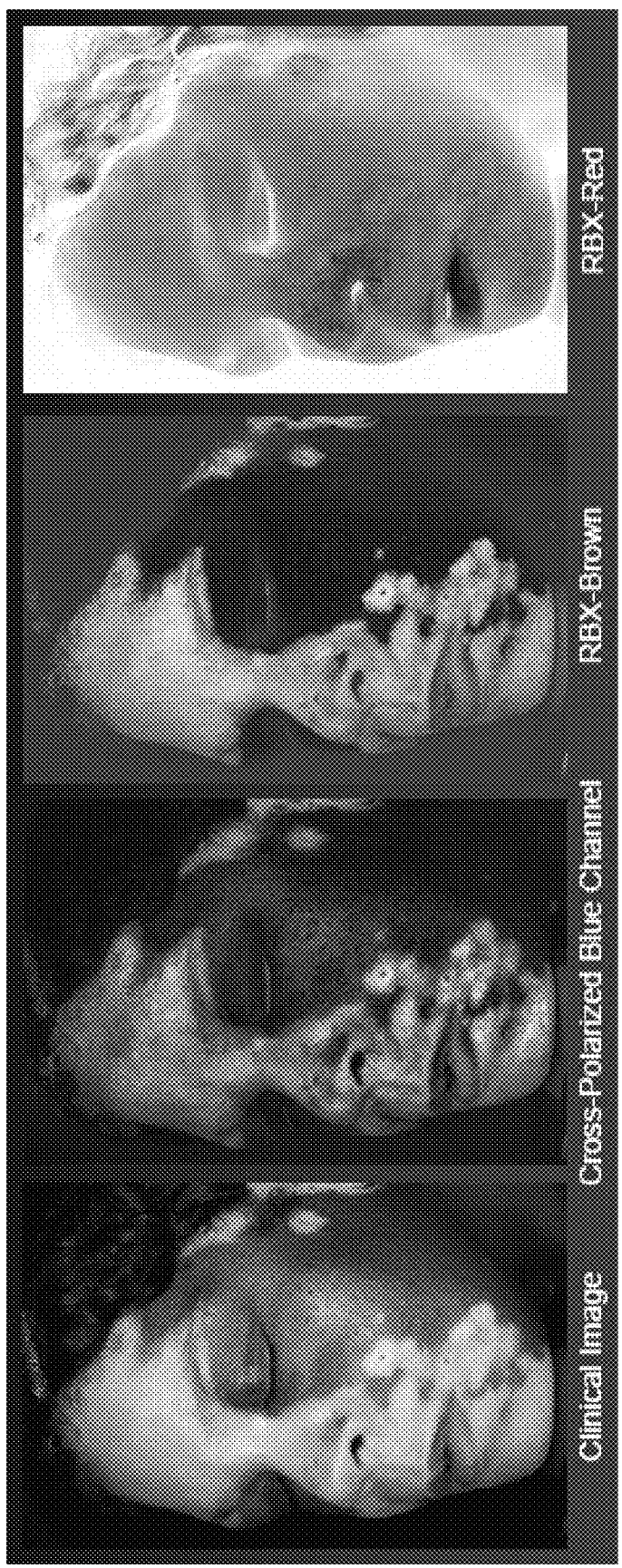
FIGS. 7A-7D show a further group of images of the first subject obtained in accordance with the present disclosure.

FIGS. 7C and 7D show the Brown and Red components, respectively, of an RBX-processed, cross-polarized RGB image (not shown) corresponding to the clinical RGB image shown in FIG. 7A. FIG. 7B shows the corresponding blue channel of the cross-polarized RGB image. It should be noted that while the RBX transformation can be performed on the clinical RGB image of FIG. 7A, a cross-polarized RGB image is preferable.

At 250, depigmented, pigmented, and areas re-pigmented due to treatment can be segmented using the input image data as transformed at 235. Such a segmentation can be performed on the RBX-Brown image of FIG. 7C, and can be carried out as described above for method 200A.

Operation then proceeds with 260-280, as described above for method 200A.

An exemplary method 200C in accordance with the present disclosure will now be described with reference to FIG. 2C, which shows a flowchart of method 200C.

Figure 2C:
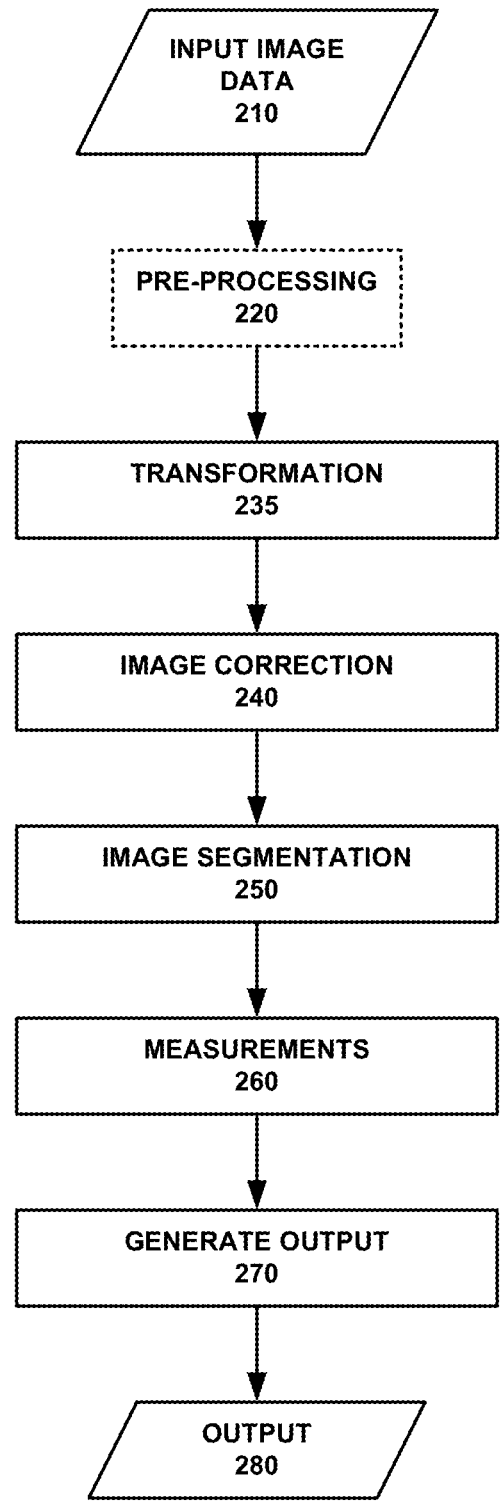

As shown in FIG. 2C, input image data is obtained at 210. A cross-polarized, narrow band blue image, such as that of FIG. 3D, is preferably included as input image data at 210 of method 200C. Additionally, input image data 210 includes a broad spectrum (white-light, RGB) cross-polarized image, such as that of FIG. 6B, corresponding to the cross-polarized, narrow-band blue image. Instead of the narrow band blue image, the blue channel of the broad-spectrum cross-polarized image, such as shown in FIG. 6C, can be used, as discussed above. While cross-polarized broad spectrum images are preferable for input image data, unpolarized broad spectrum images can be used if cross-polarized images are not available.

Returning now to the flowchart of FIG. 2C, the image data input at 210 can be pre-processed at 220 for noise removal, brightness enhancement, contrast enhancement, or the like, as described above.

After pre-processing at 220, the input image data, in particular the broad-spectrum cross-polarized image, can be subjected to one or more transformations at 235 in order to assess the distribution of pigmentation, such as due to melanin and hemoglobin. RGB input images may be transformed at 235 to other color spaces, such as the lab color space, for example, in which the a channel can be used to provide an approximation of the distribution of hemoglobin for the assessment of hemoglobin-based features.

In exemplary embodiments, an RBX transformation can be performed at 235 to obtain melanin (RBX-Brown) and/or hemoglobin (RBX-Red) distribution and concentration images can be generated from a broad-band, color cross-polarized image, such as that of FIG. 6B.

At 240, the input image data, such as the cross-polarized, narrow-band blue image of FIG. 6D or the cross-polarized blue channel image of FIG. 7B, can be corrected using one or more pigmentation images generated at 235, such as the RBX-Red image of FIG. 7D, to compensate for hemoglobin absorption where present. Although significantly less so than melanin, hemoglobin will still absorb blue color spectral band light in regions with erythema and superficial vasculature and will affect the measurement of pigmentation. At 240, correction for such absorption can be carried out by subtracting or dividing the input image by one or more of the pigmentation images generated at 235. In exemplary implementations, correction at 240 can be carried out as described, for example, in U.S. patent application Ser. No. 16/183,659, filed Nov. 7, 2018 and entitled ENHANCING PIGMENTATION IN DERMOSCOPY IMAGES, incorporated herein by reference in its entirety.

Furthermore, because hemoglobin in lighter skin tends to be more prominently visible than in darker skin, if the image to be evaluated is being corrected for hemoglobin at 240, then the amount of correction can be set based on skin type, with the degree of correction being greater for lighter skin types.

In addition, at 240, an excitation light correction operation, such as that performed at 230 of method 200A, is preferably performed on the cross-polarized, narrow-band blue image or the cross-polarized blue channel image.

At 250, depigmented, pigmented, and areas re-pigmented due to treatment can be segmented using the input image data as corrected at 240. Such a segmentation can be carried out as described above for method 200A. In addition or as an alternative to segmentation of the cross-polarized narrow-band blue or blue channel image as corrected at 240, segmentation can be performed on an RBX-Brown image generated by an RBX transformation performed at 235 on the broad spectrum image. It should be noted that if an RBX-Brown image is used for segmentation, correction for hemoglobin absorption (at 240) can be omitted because the distributions of melanin (as represented by RBX-Brown) and of hemoglobin (as represented by RBX-Red) have already been separated by virtue of the RBX transformation.

After segmentation at 250, operation proceeds with 260-280, as described above.

Figure 9:
FIG. 9 shows a first group of images of a second subject for illustrating aspects of the present disclosure.

FIG. 9 shows a first group of images of a second subject for illustrating aspects of the present disclosure. The images of FIG. 9 are analogous to those of FIGS. 3A-3D, discussed above.

Figure 10:
FIG. 10 shows a second group of images derived from the first group of images of FIG. 9.

FIG. 10 shows a second group of images derived from the first group of images shown in FIG. 9. The images of FIG. 10 are analogous to those of FIGS. 4A-4D, discussed above.

FIGS. 11A-11D show enlarged duplicates of the images of FIG. 10 enlarged to show only the region of interest (ROI) indicated in FIG. 10.

FIGS. 12A-12D show a group of images of the second subject obtained in accordance with the present disclosure. The images of FIGS. 12A-12D are analogous to those of FIGS. 6A-6D, discussed above.

FIGS. 13A-13D show a further group of images of the second subject obtained in accordance with the present disclosure. The images of FIGS. 13A-13D are analogous to those of FIGS. 7A-7D, discussed above.

Figures 13A, 13B, 13C, 13D:
FIGS. 13A-13D show a further group of images of the second subject obtained in accordance with the present disclosure.
Figure 14B:
FIG. 14B shows the processed input image further processed to indicate areas of depigmentation detected in accordance with the present disclosure.
Figure 14A:
FIG. 14A shows a processed input image.

FIG. 14A shows the RBX-Brown image also shown in FIG. 13C. FIG. 14B shows the RBX-Brown image processed to indicate areas of depigmentation detected, such as in a segmentation operation at 250, in accordance with the present disclosure. As illustrated by FIG. 14B, areas of depigmentation can be clearly detected even in cases not easily detectable by human observation, whether under white light or Wood's lamp illumination.

FIG. 15A shows a whole-body, cross-polarized white-light, three-dimensional model of a third subject captured with a VECTRA WB360 imaging system. FIG. 15B shows an image of a portion of the 3D model of FIG. 15A. FIG. 15C shows the blue channel of the image of FIG. 15B.

Figure 16:
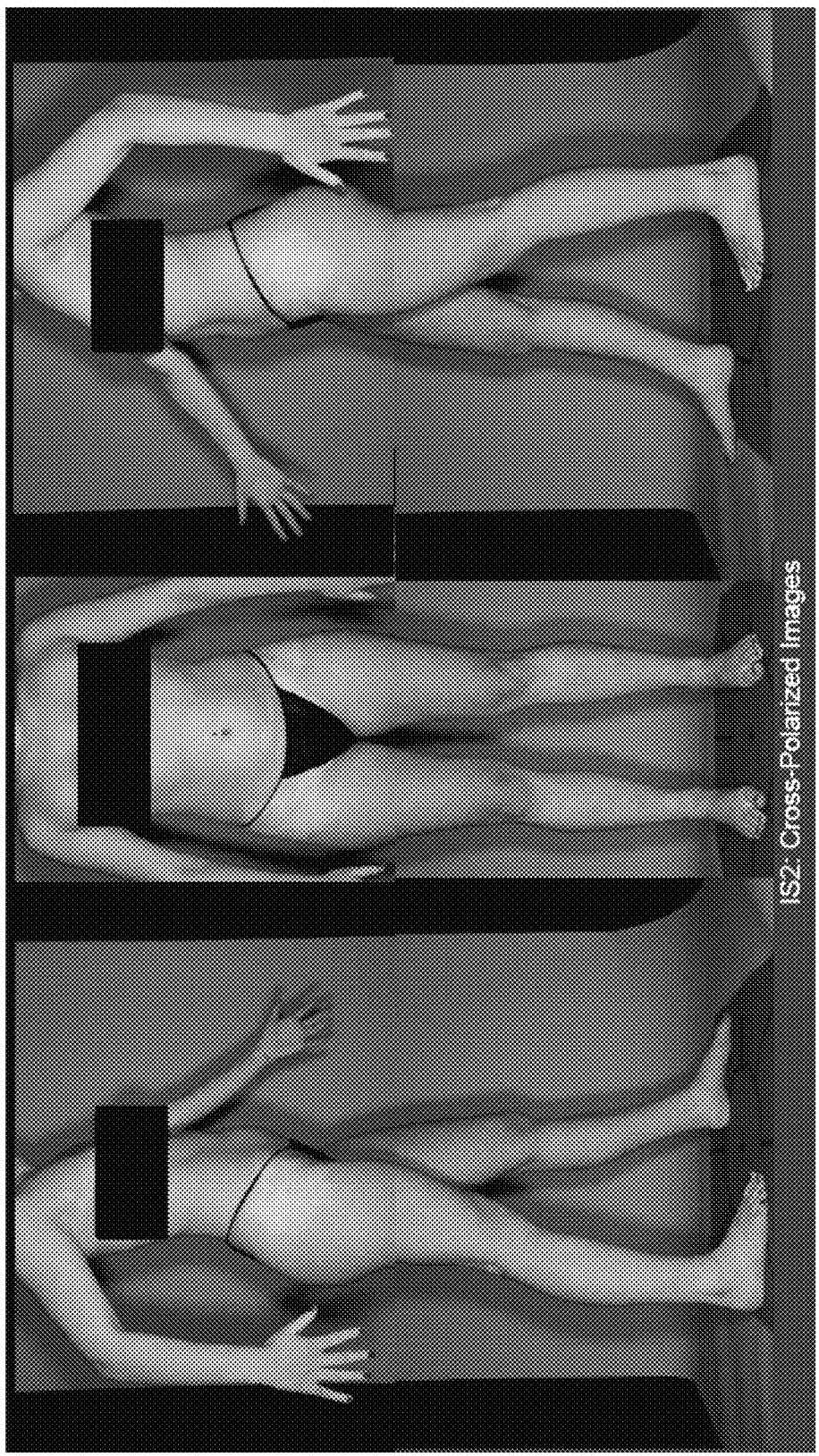
FIG. 16 shows a group of cross-polarized white-light images of a fourth subject.
Figure 17:
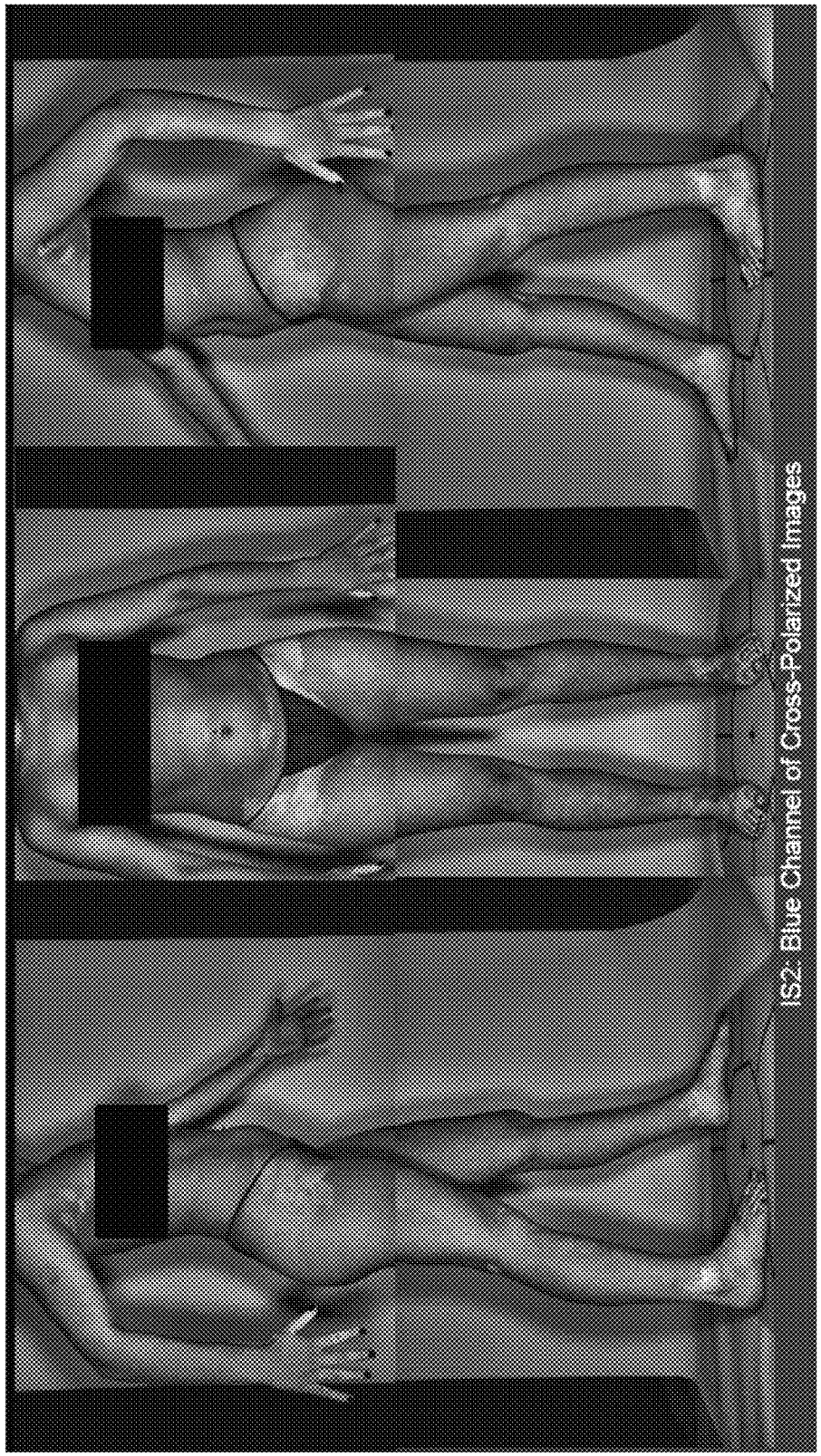
FIG. 17 shows the blue channel component images of the images of FIG. 16.
Figure 18:
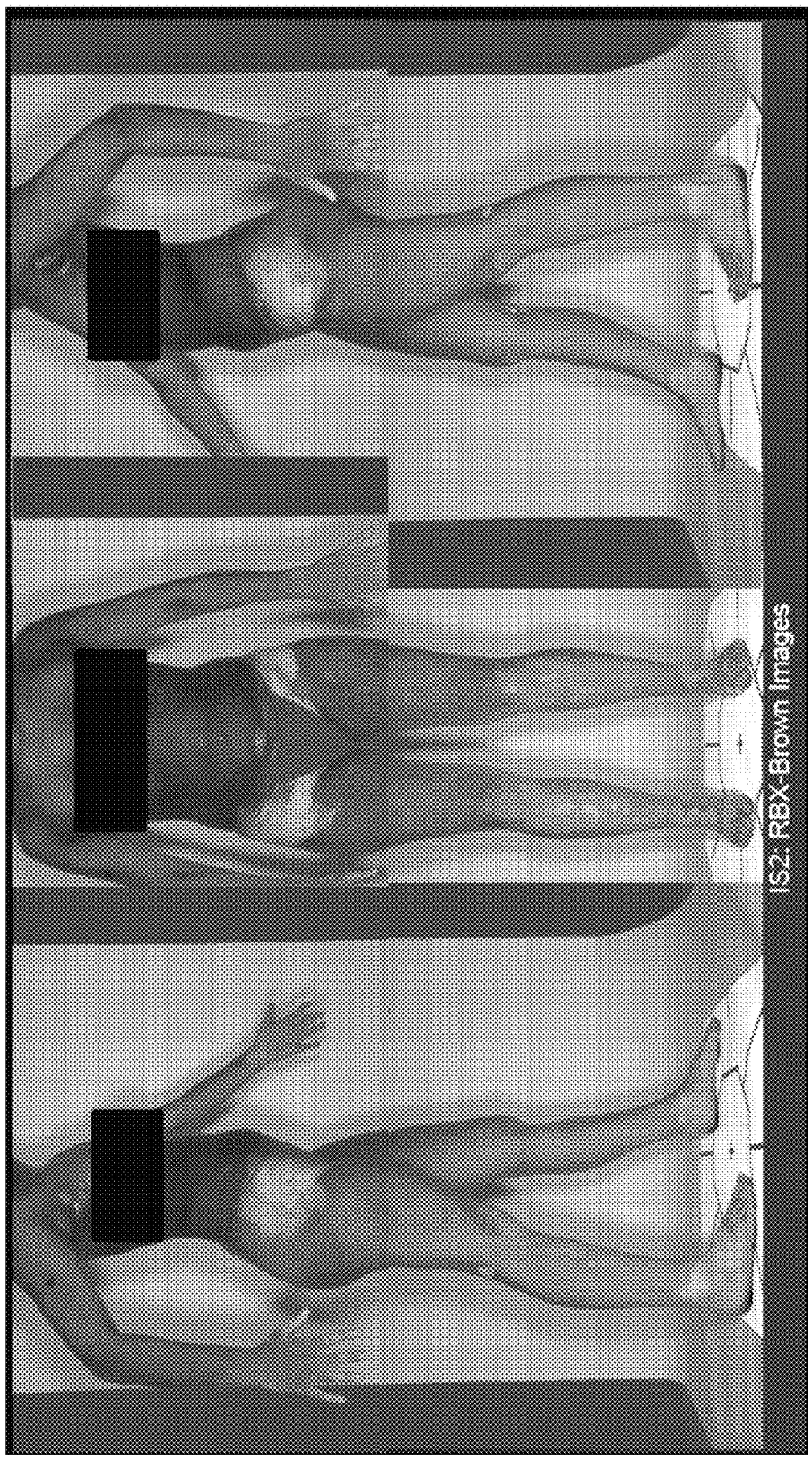
FIG. 18 shows RBX-Brown images corresponding to the images of FIGS. 16 and 17.

FIG. 16 shows a group of cross-polarized white-light images of a fourth subject captured with an INTELLISTUDIO 2 imaging system. FIG. 17 shows the blue channel of the images of FIG. 16. FIG. 18 shows the RBX-Brown images corresponding to the images of FIGS. 16 and 17.

Figure 19:
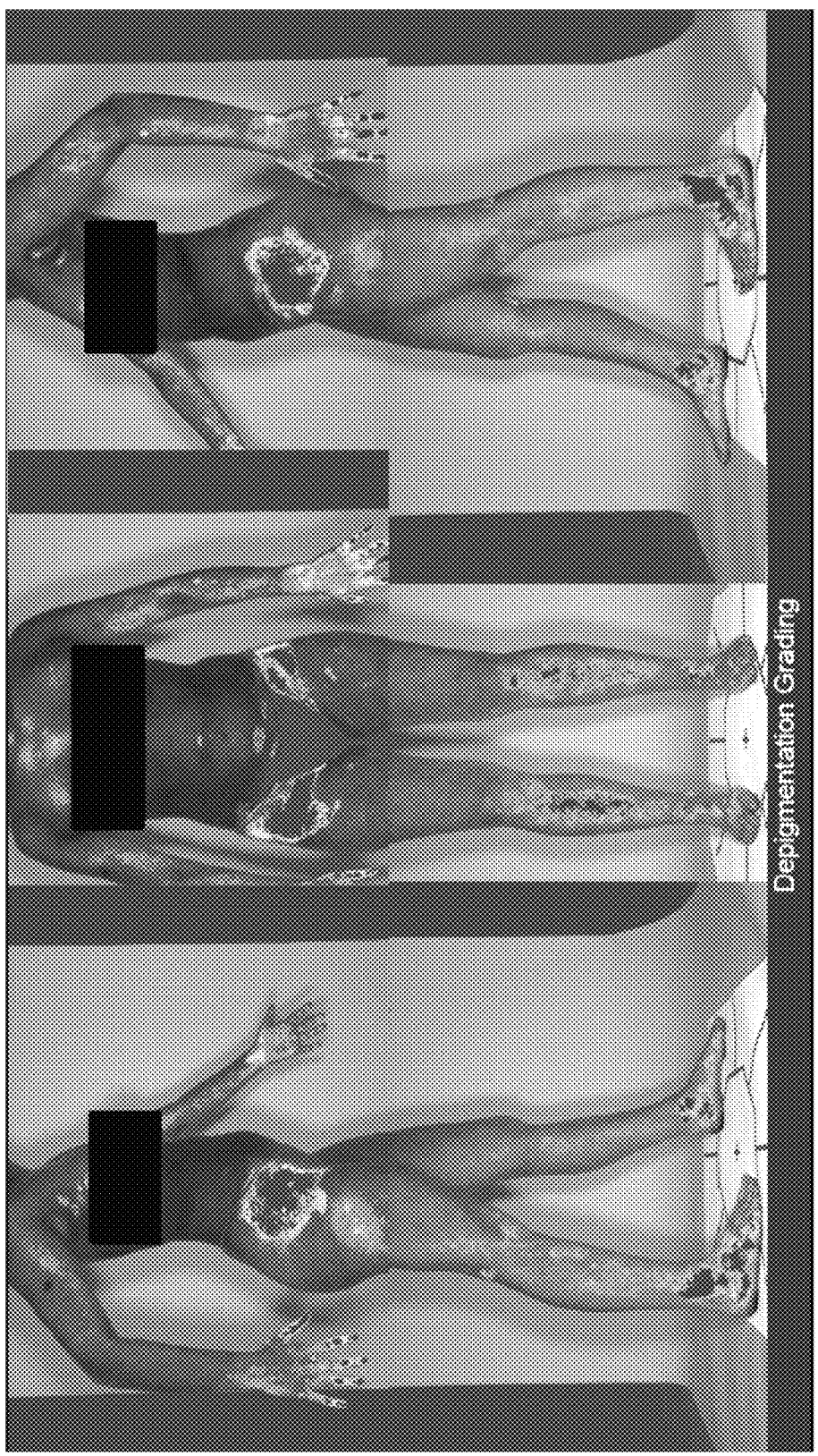
FIG. 19 shows heat map images, corresponding to the images of FIGS. 16-18, indicative of the degree of depigmentation.

FIG. 19 shows heat map images, corresponding to the images of FIGS. 16-18, indicative of the degree of depigmentation. Instead of just detecting the depigmented areas and reporting the area and/or fractional area of depigmentation, implementations in accordance with the present disclosure can also determine and indicate levels of pigmentation, such as illustrated in FIG. 19. Because most treatments will restore about 10-20% pigmentation, only reporting the area of re-pigmentation may not have the required sensitivity to properly measure treatment efficacy. Indicating pigmentation levels in addition to area, as illustrated in FIG. 19, provides a better measure of treatment efficacy.

In addition or as an alternative to fully automated detection and measurement, technician-assisted operation can be implemented in accordance with the present disclosure. For example, segmentation and measurement can be performed with input from an imaging technician who is presented the image to be analyzed. In such an implementation, a user interface is provided which allows the technician to specify the detection sensitivity, such as for example, the segmentation threshold. A slider for tuning the sensitivity may be provided, for example, and the detection in some form of an overlay may be presented to the technician when selecting the threshold/sensitivity.

At this point, while this disclosure has been presented using some specific examples, those skilled in the art will recognize that the teachings of this disclosure are not thus limited. The foregoing merely illustrates principles of the invention and it will thus be appreciated that those skilled in the art will be able to devise numerous alternative arrangements which, although not explicitly described herein, embody the principles of the invention and are within its spirit and scope. It is to be understood that numerous modifications may be made to the illustrative embodiments and that other arrangements may be devised without departing from the spirit and scope of the present invention as defined by the appended claims.

What is claimed:

1. A method of assessing pigmentation of skin comprising:
    obtaining a cross-polarized image of skin;
    determining a level of a pigment of the skin, the level of the pigment being determined in accordance with a brightness of the cross-polarized image;
    determining an area in which the brightness of the cross-polarized image is above a threshold;
    modifying the image to indicate the level of the pigment and the area, wherein the level of the pigment in the area is within one of a plurality of ranges, with pigmentation levels in each range being indicated in the modified image by at least one of a color or shade associated with the range; and
    causing the modified image to be displayed, transmitted or further processed.

2. The method of claim 1, comprising:
    generating at least one of a metric indicative of the level of the pigment or a metric indicative of the area; and
    causing the at least one metric to be displayed, stored, transmitted or further processed.

3. The method of claim 1, comprising:
    pre-processing the image before determining the level of the pigment.

4. The method of claim 1, wherein determining the level of the pigment includes performing a transformation procedure on the cross-polarized image, the level of the pigment being determined in accordance with a brightness of the transformed cross-polarized image, the transformation procedure including at least one of a color space transformation, or a Red/Brown/X transformation.

5. The method of claim 1, wherein obtaining the cross-polarized image includes:
    illuminating the area of skin with polarized light of a first orientation; and
    capturing the image through a polarized filter of a second orientation, wherein the first and second orientations are mutually orthogonal.

6. The method of claim 1, wherein the pigment includes melanin.

7. The method of claim 1, wherein the image has been captured with at least one of blue illumination or through blue filtering.

8. The method of claim 1 comprising:
    determining a hemoglobin absorption distribution of the skin; and
    correcting the cross-polarized image using the hemoglobin absorption distribution.

9. A non-transitory computer-readable storage medium having stored thereon a computer program comprising instructions for causing the skin imaging apparatus to perform the method of claim 1.

10. An apparatus for assessing pigmentation of skin comprising:
    a storage device containing instructions; and
    a processor configured to execute the instructions to:
        obtain a cross-polarized image of skin;
        determine a level of a pigment of the skin, the level of the pigment being determined in accordance with a brightness of the cross-polarized image;
        determine an area in which the brightness of the cross-polarized image is above a threshold;
        modify the image to indicate the level of the pigment and the area, wherein the level of the pigment in the area is within one of a plurality of ranges, with pigmentation levels in each range being indicated in the modified image by at least one of a color or shade associated with the range; and
        cause the modified image to be displayed, stored, transmitted or further processed.

11. The apparatus of claim 10, wherein the processor is configured to execute instructions to:
    generate at least one of a metric indicative of the level of the pigment or a metric indicative of the area; and
    cause the at least one metric to be displayed, stored, transmitted or further processed.

12. The apparatus of claim 10, wherein the processor is configured to execute instructions to:
    pre-process the image before determining the level of the pigment.

13. The apparatus of claim 10, wherein determining the level of the pigment includes performing a transformation procedure on the cross-polarized image, the level of the pigment being determined in accordance with a brightness of the transformed cross-polarized image, the transformation procedure including at least one of a color space transformation, or a Red/Brown/X transformation.

14. The apparatus of claim 10, comprising an image capture device including:
    a light source for illuminating the area of skin with polarized light of a first orientation; and
    a polarized filter of a second orientation through which the image is captured,
    wherein the first and second orientations are mutually orthogonal.

15. The apparatus of claim 10, wherein the pigment includes melanin.

16. The apparatus of claim 10, wherein the image has been captured with at least one of blue illumination or through blue filtering.

17. The apparatus of claim 10, wherein the processor is configured to execute instructions to:
    determine a hemoglobin absorption distribution of the skin; and
    correct the cross-polarized image using the hemoglobin absorption distribution.

18. The method of claim 1, wherein the threshold is determined in accordance with a type of the skin.

19. The apparatus of claim 10, wherein the threshold is determined in accordance with a type of the skin.

\* \* \* \* \*